United States Patent [19]

Aloup et al.

[11] 4,379,154
[45] * Apr. 5, 1983

[54] THIOCARBOXAMIDE DERIVATIVES AND THEIR USE AS PHARMACEUTICALS

[75] Inventors: Jean-Claude Aloup, Villeneuve-le-Roi; Jean Bouchaudon, Morsang-sur-Orge; Daniel Farge, Thiais; Claude James, Paris, all of France

[73] Assignee: Rhone-Poulenc Sante, France

[ * ] Notice: The portion of the term of this patent subsequent to Jun. 9, 1998, has been disclaimed.

[21] Appl. No.: 264,550

[22] Filed: May 18, 1981

[30] Foreign Application Priority Data

Aug. 18, 1980 [FR] France .................. 80 18035

[51] Int. Cl.³ .................. A61K 31/50; C07D 237/08
[52] U.S. Cl. .................. 424/250; 424/251; 424/258; 424/263; 424/273 R; 544/238; 544/283; 544/335; 544/336; 544/353; 546/122; 546/176; 546/268; 546/283; 546/284; 548/336
[58] Field of Search .............. 546/122, 176, 268, 284, 546/283; 544/238, 283, 336, 335, 353; 548/336; 424/250, 251, 258, 263, 273 R

[56] References Cited

U.S. PATENT DOCUMENTS 4,272,534 6/1981 Aloup et al. .................. 546/284

Primary Examiner—Henry R. Jiles
Assistant Examiner—Bernard Dentz
Attorney, Agent, or Firm—Stevens, Davis, Miller & Mosher

[57] ABSTRACT

Thioformamide derivatives of the formula:

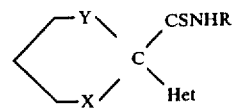

wherein R represents hydrogen or alkyl of 1 through 4 carbon atoms, and (i) Het represents a heterocyclic radical selected from pyrid-3-yl, pyrid-4-yl, pyridazinyl, pyrazinyl, pyrimidinyl, quinolyl, imidazolyl, naphthyridinyl, quinoxalinyl and quinazolinyl, X represents sulphur or oxygen and Y represents sulphur or oxygen, a valency bond or methylene, or (ii) Het represents pyrid-2-yl, X represents sulphur or oxygen and Y represents sulphur or oxygen or methylene, or (iii) Het represents pyrid-2-yl, X represents oxygen and Y represents a valency bond, are new compounds possessing useful pharmacological properties. They are particularly useful in the treatment of gastrointestinal ulcers and in the treatment of hypertension, depending on the definition of the symbol Het.

19 Claims, No Drawings

THIOCARBOXAMIDE DERIVATIVES AND THEIR USE AS PHARMACEUTICALS

DESCRIPTION

This invention relates to new therapeutically useful thioformamide derivatives, to processes for their preparation and to pharmaceutical compositions containing them.

The thioformamide derivatives of the present invention are those compounds of the general formula:

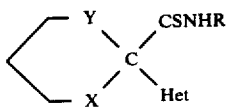

wherein R represents a hydrogen atom or a straight- or branched-chain alkyl radical containing 1 to 4 carbon atoms (preferably methyl), and (i) Het represents a heterocyclic radical of aromatic character, containing one or two nitrogen atoms, selected from pyrid-3-yl, pyrid-4-yl, pyridazinyl, pyrazinyl, pyrimidinyl, quinolyl, imidazolyl, naphthyridinyl, quinoxalinyl and quinazolinyl, X represents a sulphur or oxygen atom and Y represents a sulphur or oxygen atom, a valency bond or a methylene radical, or (ii) Het represents the pyrid-2-yl radical, X represents a sulphur or oxygen atom and Y represents a sulphur or oxygen atom or a methylene radical, or (iii) Het represents the pyrid-2-yl radical, X represents an oxygen atom and Y represents a valency bond.

Derivatives of thioacetamide and of heterocyclylalkanethiocarboxylic acids, which inhibit gastric secretion, have already been disclosed in inter alia French Patent Applications published under Nos. 2100970 and 2258178, and British Patent No. 1351024 which corresponds to French Application No. 2100970. None of these documents describes or suggests the products of the general formula I wherein X and Y are as defined above.

According to a feature of the present invention, the thioformamide derivatives of general formula I, wherein the symbols R, Het, X and Y are as defined above, are prepared by the process which comprises reacting ammonia or an amine of the general formula:

$$R-NH_2 \qquad II$$

(wherein R is as defined as above) with a dithioester of the general formula:

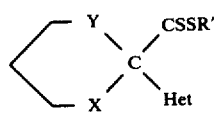

wherein the symbols Het, X and Y are as hereinbefore defined, and R' represents a straight- or branched-chain alkyl radical containing 1 to 4 carbon atoms, or a benzyl or carboxymethyl radical.

In general, the reaction is carried out with an excess of ammonia or an amine of general formula II, without a solvent or in an organic solvent, such as an aromatic hydrocarbon, an ether or an alcohol of low molecular weight, or a mixture of these solvents, at a temperature between 20° and 130° C., optionally under pressure.

The dithioesters of general formula III can be obtained by reacting an organo-lithium derivative with a heterocyclic compound of the general formula:

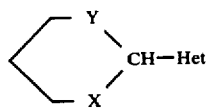

(wherein Het, X and Y are as hereinbefore defined), followed by reacting the resulting product with carbon disulphide and then with a compound of the general formula:

$$R'-Z \qquad V$$

wherein R' is as hereinbefore defined, and Z represents a halogen atom, preferably a chlorine, bromine or iodine atom, or a reactive ester radical, preferably a mesyloxy or tosyloxy radical.

The reaction is generally carried out in an anhydrous organic solvent, such as hexamethylphosphorotriamide, to which an ether, such as tetrahydrofuran, has generally been added, at a temperature between −80° and −40° C.

The organo-lithium derivatives which are particularly suitable are preferably alkyllithium compounds, such as butyllithium and isopropyllithium, or phenyllithium, dissolved in an inert solvent, such as hexane, or a lithium amide, such as lithium diethylamide or lithium diisopropylamide.

Depending on the definitions of X and Y, the heterocyclic compounds of general formula IV can be prepared as follows:

(a) The compounds of general formula IV wherein either (i) Het is a radical Het₁ representing a heterocyclic radical of aromatic character, containing one or two nitrogen atoms, selected from pyrid-3-yl, pyrid-4-yl, pyridazinyl, pyrazinyl, pyrimidinyl, quinolyl, imidazolyl, naphthyridinyl, quinoxalinyl and quinazolinyl, X represents a sulphur atom and Y represents a valency bond or a methylene radical, i.e. compounds of the general formula:

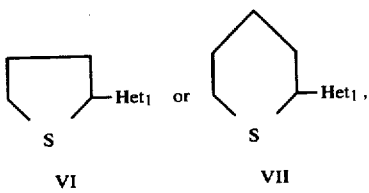

or (ii) Het represents the pyrid-2-yl radical, X represents a sulphur atom and Y represents a methylene radical, i.e. the compound of the formula:

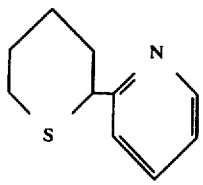

can be prepared by the cyclisation by means of an organic base, such as an alkali metal alkoxide or amide, of a heterocyclic derivative of the general formula:

Het$_2$-CH$_2$S(CH$_2$)$_3$-Y-Z°    IX (wherein Het$_2$ represents a radical Het$_1$ as hereinbefore defined, or the pyrid-2-yl radical, X and Y are as just defined above, and Z° represents a halogen atom, preferably a chlorine or bromine atom, or a reactive ester radical, preferably a mesyloxy or tosyloxy radical), the cyclisation of the compound of general formula IX being carried out in an anhydrous organic solvent, such as tetrahydrofuran or hexamethylphophorotriamide, or a mixture of these solvents, at a temperature between −80° and +25° C. Potassium tert.-butoxide, lithium diethylamide or lithium diisopropylamide is particularly advantageously used as the organic base.

The heterocyclic derivative of general formula IX can be obtained by the alkaline hydrolysis (preferably by means of an aqueous solution of an alkali metal hydroxide, such as sodium hydroxide) of an acid addition salt of an isothiourea of the general formula:

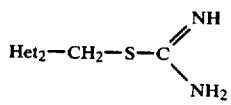

(wherein Het$_2$ is as hereinbefore defined) at a temperature between 50° C. and the boiling point of the reaction mixture, followed by reaction with a compound of the general formula:

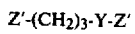

Z'-(CH$_2$)$_3$-Y-Z'    XI (wherein Y is as defined above, and the symbols Z', which may be the same or different, each represent a halogen atom, preferably a chlorine or bromine atom, or a reactive ester radical, preferably a mesyloxy or tosyloxy radical) at a temperature of the order of 20° C., in the presence of an alkali metal hydroxide, such as sodium hydroxide.

It is possible to isolate, as an intermediate, the heterocyclic derivative of the general formula:

Het$_2$-CH$_2$-SH    XII (Het$_2$ being as hereinbefore defined), originating from the alkaline hydrolysis of the isothiourea of general formula X, and then to react the thiol with the compound of general formula XI in the presence of an alkali metal hydroxide, such as sodium hydroxide.

The isothioureas of the general formula X, in the form of acid addition salts, such as the hydrochlorides, can be obtained by reacting thiourea with a heterocyclic derivative of the general formula:

Het$_2$-CH$_2$-Z''    XIII (wherein Z'' represents a halogen atom, preferably a chlorine or bromine atom), optionally in the form of an acid addition salt such as a hydrohalide, the reaction being carried out in an organic solvent, such as an alcohol (e.g. ethanol), at the reflux temperature of the reaction mixture.

The heterocyclic derivatives of general formula XIII can be prepared, according to the selected heterocyclic compound, by employing the method of W. Mathes and H. Schuly, Angew. Chem. Intern. Ed. 2, 144 (1963), or the method of H. S. Mosher and J. E. Tessieri, J. Amer. Chem. Soc., 73, 4925 (1957), or also the methods of K. Y. Novotskii et al., Khim. Geterotsikl. Soedin., (3), 412 (1970); C.A., 73, 25385z (1970), or of A. Hirschberg and P. E. Spoerri, J. Org. Chem., 26 2356 (1961).

(a) The compounds of general formula IV wherein Het is as hereinbefore defined, X represents a sulphur or oxygen atom and Y represents a sulphur or oxygen atom, can be prepared by reacting a compound of the general formula:

HX-(CH$_2$)$_3$-Y-H    XIV (wherein X and Y are as just defined) with an aldehyde of the general formula:

Het-CHO    XV (wherein Het is as hereinbefore defined) in a solvent which makes it possible to remove, by azeotropic distillation, the water formed during the reaction. In practice, it is preferred to use benzene, toluene, a xylene or 1,2-dichloroethane as solvent.

(c) The compounds of general formula IV wherein Het is as hereinbefore defined, X represents an oxygen atom and Y represents a valency bond or a methylene radical, can be prepared by cyclising a compound of the general formula:

Het-CHOH(CH$_2$)$_n$-O-R''    XVI wherein Het is as hereinbefore defined, R'' represents a radical for protecting an alcohol function such as a t-butyl, t-pentyl or tetrahydropyranyl radical, and n represents 3 or 4. The reaction is generally carried out by heating under reflux in an organic solvent, such as toluene, in the presence of paratoluenesulphonic acid; this treatment can optionally be followed by heating in polyphosphoric acid at a temperature between 50° and 120° C.

The compounds of general formula XVI can be prepared by reacting a magnesium derivative of the general formula:

Z'''Mg-(CH$_2$)$_n$-O-R''    XVII (wherein R'' and n are as hereinbefore defined, and Z''' represents a halogen atom such as a bromine or iodine atom) with an aldehyde of general formula XV, the reaction being carried out analogously to the method described by W. B. Renfrow, J. Org. Chem. 26, 935 (1961).

According to another feature of the present invention, the thioformamide derivatives of general formula I wherein Het, X and Y are as hereinbefore defined and R represents a straight or branched-chain alkyl radical containing 1 to 4 carbon atoms, are prepared by the process which comprises reacting an organo-lithium derivative with a heterocyclic compound of general formula IV, followed by reacting the resulting compound with an isothiocyanate of the general formula:

   XVIII wherein R''' represents a straight- or branched-chain alkyl radical containing 1 to 4 carbon atoms.

The organo-lithium derivatives which are particularly suitable are preferably alkyllithium compounds, such as butyllithium and isopropyllithium, or phenyllithium, dissolved in an inert organic solvent such as hexane, or lithium amides, such as lithium diethylamide or lithium diisopropylamide.

If, as has been stated above under (a), the heterocyclic compound of general formula IV is obtained from a compound of general formula IX and an alkali metal amide, it is not necessary to isolate the product of general formula IV before reacting it with the isothiocyanate of general formula XVIII. It suffices to employ two equivalents of amide.

The reaction is generally carried out in an anhydrous organic solvent, such as hexamethylphosphorotriamide, to which an ether, such as tetrahydrofuran, has generally been added, at a temperature between −80° and −40° C.

The thioformamide derivatives of general formula I obtained by the aforedescribed processes can be purified by the usual physical methods, in particular crystallisation and chromatography.

The thioformamide derivatives of the present invention possess particularly useful pharmacological properties, coupled with a low toxicity. They exhibit an anti-ulcer action and an anti-secretory action. These properties can be demonstrated on rats with doses between 1 and 100 mg/kg animal body weight, administered orally, in particular using the technique of Rossi et al., C.R. Soc. Biol., 150, 2124 (1956), and the technique of Shay et al., Gastroenterology, 5, 43 (1945). Their lethal dose ($LD_{50}$) in mice is generally more than 300 mg/kg animal body weight, administered orally.

The thioformamide derivatives of general formula I which more particularly possess anti-ulcer properties are those in which Het represents a heterocyclic radical of aromatic character, containing one or two nitrogen atoms, which is attached in the α-position to this (or one of these) nitrogen atom (or atoms) and is selected from pyridazin-3-yl, pyrazinyl, pyrimidin-2-yl or -4-yl, quinol-2-yl, imidazol-2-yl or -4-yl, 1,8-naphthyridin-2-yl, quinoxalin-2-yl or quinazolin-2-yl or -4-yl, X represents a sulphur or oxygen atom and Y represents a sulphur or oxygen atom, a valency bond or a methylene radical, or Het represents the pyrid-2-yl radical, X represents a sulphur or oxygen atom and Y represents a sulphur or oxygen atom or a methylene radical, or Het represents the pyrid-2-yl radical, X represents an oxygen atom and Y represents a valency bond.

The thioformamide derivatives of general formula I which one more especially valuable as anti-ulcer agents are those in which the symbol Het as it has just been defined, represents the pyrid-2-yl, quinol-2-yl or pyridazin-3-yl radical.

The following compounds are very particularly valuable: N-methyl-2-(quinol-2-yl)-tetrahydrothiophen-2-carbothioamide, N-methyl-2-(pyrid-2-yl)-tetrahydrothiopyran-2-carbothioamide, N-methyl-2-(pyrid-2-yl)-1,3-dithiane-2-carbothioamide, N-methyl-2-(pyrid-2-yl)-tetrahydrofuran-2-carbothioamide, 2-(pyrid-2-yl)-1,3-dithiane-2-carbothioamide and N-methyl-2-(pyridazin-3-yl)-tetrahydrothiophen-2-carbothioamide.

Furthermore, the thioformamide derivatives of general formula I wherein Het represents a heterocyclic radical of aromatic character, containing one or two nitrogen atoms, which is attached in the β-position to this (or one of these) nitrogen atom (or atoms) and is selected from pyrid-3-yl, pyridazin-4-yl, pyrimidin-5-yl, quinol-3-yl, imidazol-5-yl and 1,8-naphthyridin-3-yl, X represents a sulphur or oxygen atom and Y represents a sulphur or oxygen atom, a valency bond or a methylene radical, are more particularly active as regulators of the cardiovascular system, in particular as anti-hypertensive agents. At doses between 0.1 and 100 mg/kg animal body weight, administered orally, they lower the blood pressure of spontaneously hypertensive rats (SHR) of the Okamoto-Aoki strain. The use of spontaneously hypertensive rats for studying anti-hypertensive products is described by J. L. Roba, Lab. Anim. Sci., 26, 305 (1976).

The thioformamide derivatives of general formula I which are more especially valuable as antihypertensive agents are those in which the symbol Het represents the pyrid-3-yl or quinol-3-yl radical.

The following are very particularly valuable as antihypertensive agents: N-methyl-2-(pyrid-3-yl)-tetrahydrothiophen-2-carbothioamide, N-methyl-2-(pyrid-3-yl)-tetrahydrothiopyran-2-carbothioamide, N-methyl-2-(pyrid-3-yl)-1,3-oxathiane-2-carbothioamide and N-methyl-2-(quinol-3-yl)-tetrahydrothiophen-2-carbothioamide.

The following Examples illustrate the preparation of the thioformamide derivatives of the present invention.

In the Examples the chromatography was carried out with silica having a particle size of 0.063-0.20 mm or alumina having a particle size of 0.125-0.15 mm.

EXAMPLE 1

A 33% (weight/volume) solution of methylamine in ethanol (11 cc) is added dropwise, in the course of 5 minutes, to a solution of methyl 2-(pyrid-3-yl)-tetrahydrothiophen-2-carbodithioate (14.3 g) in ethanol (50 cc), kept at a temperature of about 20° C. The solution is subsequently stirred for 5 hours at the same temperature and then cooled to 0° C. The resulting crystals are filtered off, washed with ethanol (8 cc) and then twice with diisopropyl ether (20 cc in total) and dried under reduced pressure (20 mm Hg; 2.7 kPa) at 20° C. The product thus obtained (7.2 g) is dissolved in boiling ethanol (35 cc); decolourising charcoal (0.4 g) is added to the solution, which is filtered hot, and the filtrate is then cooled for 1 hour at a temperature of about 5° C. The resulting crystals are filtered off, washed with ethanol (5 cc) and then twice with diisopropyl ether (14 cc in total) and dried under reduced pressure (1 mm Hg; 0.13 kPa) at 40° C. N-Methyl-2-(pyrid-3-yl)-tetrahydrothiophen-2-carbothioamide (5.8 g), melting at 133° C., is thus obtained.

Methyl 2-(pyrid-3-yl)-tetrahyrothiophen-2-carbodithioate can be prepared in the following manner:

A mixture of anhydrous hexamethylphosphorotriamide and anhydrous tetrahydrofuran (47/53 by volume; 125 cc) is added dropwise, in the course of 15 minutes, to a 1.6 M solution of n-butyllithium in hexane (170 cc), kept under an argon atmosphere and cooled to −50° C. A solution of 2-(pyrid-3-yl)-tetrahydrothiophen (30 g) in a mixture of anhydrous hexamethylphosphorotriamide and anhydrous tetrahydrofuran (47/53 by volume;

125 cc) is then added in the course of 10 minutes and at −60° C. After stirring for 15 minutes at −65° C., a solution of carbon disulphide (20.7 g) in a mixture of anhydrous hexamethylphosphorotriamide and anhydrous tetrahyrofuran (47/53 by volume; 16.5 cc) is added in the course of 15 minutes. After stirring for 5 minutes at −65° C., a solution of methyl iodide (38.6 g) in a mixture of anhydrous hexamethylphosphorotriamide and anhydrous tetrahydrofuran (47/53 by volume; 125 cc) is added in the course of 15 minutes at −65° C. The reaction mixture is subsequently stirred for 45 minutes at this same temperature and then for 1 hour whilst allowing the temperature to rise gradually to 0° C. After adding distilled water (1000 cc), the reaction mixture is extracted twice with ethyl acetate (950 cc in total). The organic extracts are combined and washed three times with distilled water (3000 cc in total). After drying over anhydrous sodium sulphate, filtering and concentrating to dryness under reduced pressure (20 mm Hg; 2.7 kPa) at 60° C., a brown oil (56.9 g) is obtained, which is chromatographed on neutral silica gel (550 g) contained in a column of diameter 5.4 cm. Elution is carried out with a cyclohexane/ethyl acetate mixture (95/5 by volume; 18 liters). 1000 cc fractions being collected. Fractions 8 to 18 are combined and concentrated to dryness under reduced pressure (20 mm Hg; 2.7 kPa) at 70° C. Methyl 2-(pyrid-3-yl)-tetrahydrothiophen-2-carbodithioate (19.6 g) is thus obtained in the form of a limpid orange oil.

[Rf=0.50; chromatography on a thin layer of silica gel; solvent: cyclohexane/ethyl acetate (50/50 by volume)].

2-(Pyrid-3-yl)-tetrahydrothiophen can be prepared in the following manner:

A solution of pyrid-3-yl-methyl 3-chloropropyl sulphide (59 g) in anhydrous tetrahydrofuran (75 cc) is added dropwise, in the course of 15 minutes and whilst keeping the temperature below 32° C. to a solution of potassium tert.-butoxide (50.8 g) in a mixture of anhydrous hexamethylphosphorotriamide (77 cc) and anhydrous tetrahydrofuran (410 cc). After stirring for 1 hour at a temperature of about 20° C. the reaction mixture is added to a mixture of distilled water (750 cc) and diethyl ether (420 cc). After decantation, the aqueous phase is re-extracted with diethyl ether (200 cc). The combined ether phases are washed three times with distilled water (2100 cc in total), dried over anhydrous magnesium sulphate and filtered and the filtrate is concentrated to dryness under reduced pressure (20 mm Hg; 2.7 kPa) at 45° C. 2-(Pyrid-3-yl)-tetrahydrothiophen (30 g) is thus obtained in the form of a brown oil.

[Rf=0.36; chromatography on a thin layer of silica gel; solvent: ethyl acetate/cyclohexane (50/50 by volume)].

Pyrid-3-yl-methyl 3-chloropropyl sulphide can be prepared in the following manner:

A 10 N aqueous solution of sodium hydroxide (50 cc) is added, in the course of 10 minutes and whilst allowing the temperature to rise to 14° C. to a solution, cooled to 12° C. of 2-(pyrid-3-yl-methyl)isothiourea monohydrochloride (100 g) in distilled water (250 cc). After heating for 30 minutes at a temperature of 100° C. and then cooling to 12° C. a 10 N aqueous solution of sodium hydroxide (60 cc) is added dropwise and in the course of 10 minutes. 1-Bromo-3-chloropropane (82 g) is then added, whilst stirring, and stirring is continued for 20 hours at a temperature of about 20° C. The reaction mixture is then extracted three times with methylene chloride (430 cc in total). The organic extracts are combined and washed with distilled water (250 cc) and then dried over anhydrous magnesium sulphate. After filtration, the solution obtained is poured onto neutral silica gel (100 g) contained in a column of diameter 3 cm; the column is then eluted with methylene chloride (2300 cc). The first fraction (700 cc) is discarded; the second fraction (1600 cc) is collected and concentrated to dryness under reduced pressure (20 mm Hg; 2.7 kPa) at 35° C. Pyrid-3-yl-methyl 3-chloropropyl sulphide (59 g) is thus obtained in the form of a yellow oil.

[Rf=0.33; chromatography on a thin layer of silica gel; solvent: ethyl acetate/cyclohexane (50/50 by volume)].

2-(Pyrid-3-yl-methyl)-isothiourea monohydrochloride can be prepared in the following manner:

A solution of 3-chloromethylpyridine hydrochloride (100 g) in ethanol (310 cc), at 60° C. is added dropwise and in the course of 15 minutes to a suspension of thiourea (55 g) in boiling ethanol (310 cc). The reaction mixture is stirred for 1 hour 45 minutes at the boil and then cooled to 30° C. After decantation, the supernatant solution is discarded. Ethanol (400 cc) is added to the remaining gummy solid and the mixture is stirred for 63 hours at a temperature of about 20° C. The resulting crystals are filtered off, washed twice with ethanol (60 cc in total) and dried under reduced pressure (20 mm Hg; 2.7 kPa) at a temperature of about 20° C. 2-(Pyrid-3-yl-methyl)isothiourea monohydrochloride (100 g), melting at 220° C. is thus obtained.

EXAMPLE 2

A 33% (weight/volume) solution of methylamine in ethanol (12 cc) is added dropwise, in the course of 15 minutes, to a solution of methyl 2-(pyrid-4-yl)-tetrahydrothiophen-2-carbodithioate (16 g) in ethanol (35 cc), kept at 20° C. The solution is subsequently stirred for 1 hour at a temperature of about 20° C. and is then cooled to 0° C. The resulting crystals are filtered off, washed twice with ethanol (30 cc in total) and dried under reduced pressure (20 mm Hg; 2.7 kPa) at a temperature of about 20° C. A crystalline crude product (11 g) is thus obtained, which is redissolved in boiling ethanol (100 cc); decolourising charcoal (0.3 g) is added to the solution obtained, which is filtered hot, and the filtrate is then cooled for one hour at 0° C. The resulting crystals are filtered off, washed twice with ethanol (20 cc in total) and dried under reduced pressure (20 mm Hg; 2.7 kPa) at a temperature of about 20° C. The product thus obtained (9 g) is chromatographed on neutral silica gel (20 g) contained in a column of diameter 1.7 cm. Elution is carried out with methylene chloride (1000 cc) and then with a methylene chloride/ethanol mixture (90/10 by volume; 250 cc), 250 cc fractions being collected. Fractions 1 to 5 are combined and concentrated to dryness under reduced pressure (20 mm Hg; 2.7 kPa) at 50° C. The product thus obtained (8 g) is dissolved in boiling ethanol (94 cc); decolourising charcoal (0.4 g) is added to the solution, which is filtered hot, and the filtrate is then cooled for 15 hours at a temperature of about 5° C. The resulting crystals are filtered off, washed twice with ethanol (14 cc in total) and dried under reduced pressure (20 mm Hg; 2.7 kPa) at a temperature of about 20° C. The product thus obtained (6.9 g) is dissolved in boiling acetonitrile (75 cc) and the solution, to which decolourising charcoal (0.2 g) is added, is filtered hot and the filtrate is then cooled for 1 hour at 0° C. The resulting crystals are filtered off, washed with acetonitrile (7 cc) and dried under reduced pressure (1 mm Hg; 0.13 kPa) at 60° C. N-Methyl-2-(pyrid-4-yl)-tetrahydrothiophen-2-carbothioamide (5.9 g), melting at 178° C., is thus obtained.

Methyl 2-(pyrid-4-yl)-tetrahydrothiophen-2-carbodithioate can be prepared in the following manner:

A mixture of anhydrous hexamethylphosphorotriamide and anhydrous tetrahydrofuran (47/53 by volume; 192 cc) is added dropwise and in the course of 15 minutes to a 1.6 M solution of n-butyllithium in hexane (265 cc), kept under a nitrogen atmosphere and at a temperature of about −60° C. A solution of 2-(pyrid-4-yl)-tetrahydrothiophen (46.7 g) in a mixture of anhydrous hexamethylphosphorotriamide and anhydrous tetrahydrofuran (47/53 by volume; 192 cc) is then added in the course of 20 minutes. After stirring for 20 minutes at the same temperature, a solution of carbon disulphide (32 g) in a mixture of anhydrous hexamethylphosphorotriamide and anhydrous tetrahydrofuran (47/53 by volume; 192 cc) is added in the course of 20 minutes. After stirring for 5 minutes at the same temperature, a solution of methyl iodide (60.5 g) in a mixture of anhydrous hexamethylphosphorotriamide and anhydrous tetrahydrofuran (47/53 by volume; 192 cc) is added in the course of 15 minutes. The reaction mixture is subsequently stirred for 45 minutes at −60° C. and then for 25 minutes, whilst allowing the temperature to rise gradually to 5° C. It is then run into a mixture of distilled water (1500 cc) and ethyl acetate (900 cc). After decantation, the aqueous solution is extracted with ethyl acetate (500 cc). The organic phases are combined and washed three times with distilled water (4500 cc in total) and then twice with a 2 N aqueous solution of hydrochloric acid (250 cc in total). The organic extracts are discarded; the aqueous extracts are washed twice with ethyl acetate (300 cc in total) and then neutralised to pH 8 by adding sodium bicarbonate; they are extracted three times with ethyl acetate (600 cc in total). These new organic extracts are combined and washed three times with distilled water (600 cc in total), dried over anhydrous sodium sulphate and filtered and the filtrate is concentrated to dryness under reduced pressure (20 mm Hg; 2.7 kPa) at 50° C. The product obtained (58 g) is chromatographed on neutral silica gel (450 g) contained in a column of diameter 5 cm; the column is then eluted with a cyclohexane/ethyl acetate mixture (95/5 by volume; 1500 cc), with a cyclohexane/ethyl acetate mixture (90/10 by volume; 4000 cc), with a cyclohexane/ethyl acetate mixture (85/15 by volume; 2000 cc) and with a cyclohexane/ethyl acetate mixture (80/20 by volume; 2500 cc), 500 cc fractions being collected. Fractions 10 to 12 are combined and concentrated to dryness (20 mm Hg; 2.7 kPa) at 50° C. and the partially crystalline product obtained (10 g) is filtered off, washed twice with diisopropyl ether (30 cc in total) and dried under reduced pressure (20 mm Hg; 2.7 kPa) at a temperature of about 20° C.; a first batch of product (6 g) is thus obtained. Fractions 13 to 20 are combined and concentrated to dryness under reduced pressure (20 mm Hg; 2.7 kPa) at 50° C. The second batch obtained (34 g) is combined with the first batch (6 g) and the combined batch is dissolved in boiling diisopropyl ether (180 cc); decolourising charcoal (0.4 g) is added to the solution, which is filtered hot, and the filtrate is then cooled for 1 hour at 0° C. The resulting crystals are filtered off, washed twice with diisopropyl ether (52 cc in total) and dried under reduced pressure (1 mm Hg; 0.13 kPa) at 35° C. Methyl 2-(pyrid-4-yl)-tetrahydrothiophen-2-carbodithioate (28.3 g), melting at 64° C., is thus obtained.

2-(Pyrid-4-yl)-tetrahydrothiophen can be prepared in the following manner:

A solution of pyrid-4-yl-methyl 3-chloropropyl sulphide (81 g) in anhydrous tetrahydrofuran (100 cc) is added dropwise, in the course of 20 minutes and whilst keeping the temperature below 33° C., to a solution of potassium tert.-butoxide (69.5 g) in a mixture of anhydrous hexamethylphosphorotriamide (108 cc) and anhydrous tetrahydrofuran (560 cc). The reaction mixture is then stirred for 1 hour 30 minutes at a temperature of about 20° C.; it is then run into a mixture of distilled water (1000 cc) and diethyl ether (600 cc). After decantation, the aqueous phase is extracted twice with diethyl ether (400 cc in total). The ether extracts are combined, washed three times with distilled water (3000 cc in total), dried over anhydrous sodium sulphate and filtered and the filtrate is concentrated to dryness under reduced pressure (20 mm Hg; 2.7 kPa) at 40° C. 2-(Pyrid-4-yl)-tetrahydrothiophen (46.7 g) is thus obtained in the form of a brown oil.

[Rf=0.35; chromatography on a thin layer of silica gel; solvent: cyclohexane/ethyl acetate (50/50 by volume)].

Pyrid-4-yl-methyl 3-chloropropyl sulphide can be prepared in the following manner:

A 10 N aqueous solution of sodium hydroxide (97 cc) is added dropwise, in the course of 15 minutes and whilst keeping the temperature below 14° C., to a solution of 2-(pyrid-4-yl-methyl)-isothiourea dihydrochloride (116.5 g) in distilled water (240 cc). After heating for 20 minutes at 83° C. and then cooling to 12° C., a 10 N aqueous solution of sodium hydroxide (60 cc) and then 1-bromo-3-chloropropane (81.5 g) are added, whilst stirring, and stirring is continued for 15 hours at a temperature of about 20° C. The reaction mixture is then extracted three times with methylene chloride (430 cc in total); the organic extracts are combined, washed with distilled water (250 cc) and dried over anhydrous sodium sulphate. After filtration, the solution obtained is poured onto neutral silica gel (125 g) contained in a column of diameter 3.2 cm; the column is then eluted with methylene chloride (1600 cc). The first fraction (400 cc) is discarded; the second fraction (1200 cc) is collected and concentrated to dryness under reduced pressure (20 mm Hg; 2.7 kPa) at 40° C. Pyrid-4-yl-methyl 3-chloropropyl sulphide (81 g) is thus obtained in the form of a brown oil.

[Rf=0.3; chromatography on a thin layer of silica gel; solvent: cyclohexane/ethyl acetate (50/50 by volume)].

2-(Pyrid-4-yl-methyl)-isothiourea dihydrochloride can be prepared in the following manner:

A suspension of 4-chloromethylpyridine hydrochloride (82 g) in gently boiling ethanol (260 cc) is added dropwise and in the course of 30 minutes to a suspension of thiourea (45.5 g) in boiling ethanol (260 cc). The reaction mixture is stirred for 1 hour 30 minutes at the boil and then cooled to 5° C. The resulting crystals are filtered off, washed twice with ethanol (60 cc in total) and dried under reduced pressure (20 mm Hg; 2.7 kPa) at a temperature of about 20° C. 2-(Pyrid-4-yl-methyl)-isothiourea dihydrochloride (116 g), melting at 260° C., is thus obtained.

EXAMPLE 3

A 33% (weight/volume) solution of methylamine in ethanol (13.5 cc) is added dropwise and in the course of 10 minutes to a suspension of methyl 2-(quinol-2-yl)-tetrahydrothiophen-2-carbodithioate (20 g) in ethanol (42 cc), kept at a temperature of about 20° C. The reaction mixture is then stirred for 15 hours at a temperature of about 20° C. The resulting crystals are filtered off, washed twice with ethanol (24 cc in total) and dried under reduced pressure (20 mm Hg; 2.7 kPa) at a temperature of about 20° C. A crystalline crude product (12.1 g) is thus obtained. This product is redissolved in boiling ethanol (75 cc); decolourising charcoal (0.6 g) is added to the solution, which is filtered hot, and the filtrate is then cooled for 3 hours at a temperature of about 5° C. The resulting crystals are filtered off, washed twice with ethanol (24 cc in total) and dried under reduced pressure (1 mm Hg; 0.13 kPa) at 60° C. N-Methyl-2-(quinol-2-yl)-tetrahydrothiophen-2-carbothioamide (11 g), melting at 124° C., is thus obtained.

Methyl 2-(quinol-2-yl)-tetrahydrothiophen-2-carbodithioate can be prepared in the following manner:

A mixture of anhydrous hexamethylphosphorotriamide and anhydrous tetrahydrofuran (47/53 by volume; 100 cc) is added dropwise and in the course of 10 minutes to a 1.6 M solution of n-butyllithium in hexane (138 cc), kept under an argon atmosphere and at a temperature of about −60° C. A solution of 2-(quinol-2-yl)-tetrahydrothiophen (31 g) in a mixture of anhydrous hexamethylphosphorotriamide and anhydrous tetrahydrofuran (47/53 by volume; 100 cc) is then added in the course of 15 minutes. After stirring for 5 minutes, a solution of carbon disulphide (17 g) in a mixture of anhydrous hexamethylphosphorotriamide and anhydrous tetrahydrofuran (47/53 by volume; 100 cc) is added dropwise in the course of 15 minutes and at the same temperature. After stirring for 5 minutes, a solution of methyl iodide (32 g) in a mixture of anhydrous hexamethylphosphorotriamide and anhydrous tetrahydrofuran (47/53 by volume; 100 cc) is added dropwise and in the course of 25 minutes. The reaction mixture is subsequently stirred for 45 minutes at −65° C. and then for 45 minutes, whilst allowing the temperature to rise gradually to about 20° C. It is then run into a mixture of distilled water (750 cc) and ethyl acetate (450 cc). After decantation, the aqueous phase is extracted with ethyl acetate (250 cc). The organic extracts are combined, washed three times with distilled water (2250 cc in total), dried over anhydrous sodium sulphate and filtered and the filtrate is concentrated to dryness under reduced pressure (20 mm Hg; 2.7 kPa) at 70° C. The product obtained (57 g) is chromatographed on neutral silica gel (550 g) contained in a column of diameter 5.2 cm; the column is then eluted with a cyclohexane/ethyl acetate mixture (95/5 by volume; 1000 cc) and with a cyclohexane/ethyl acetate mixture (90/10 by volume; 1000 cc), 500 cc fractions being collected. Fractions 1 to 3 are combined and concentrated to dryness under reduced pressure (20 mm Hg; 2.7 kPa) at 50° C.; a crude product (36.6 g) is thus obtained. 14 g thereof are dissolved in boiling diisopropyl ether (70 cc); decolourising charcoal (0.3 g) is added to the solution, which is filtered hot, and the filtrate is then cooled for 2 hours at a temperature of about 5° C. The resulting crystals are filtered off, washed with diisopropyl ether (7 cc) and then twice with petroleum ether (30 cc in total). After drying under reduced pressure (1 mm Hg; 0.13 kPa) at 45° C., methyl 2-(quinol-2-yl)-tetrahydrothiophen-2-carbodithioate (8.9 g), melting at 72° C., is obtained.

2-(Quinol-2-yl)-tetrahydrothiophen can be prepared in the following manner:

A solution of quinol-2-yl-methyl 3-chloropropyl sulphide (82 g) in anhydrous tetrahydrofuran (100 cc) is added dropwise, in the course of 35 minutes and whilst keeping the temperature below 33° C., to a solution of potassium tert.-butoxide (56.5 g) in a mixture of anhydrous hexamethylphosphorotriamide (85 cc) and anhydrous tetrahydrofuran (455 cc). The reaction mixture is subsequently stirred for 1 hour 15 minutes at the same temperature and is then run into a mixture of distilled water (800 cc) and diethyl ether (500 cc). After decantation, the aqueous phase is extracted twice with diethyl ether (320 cc in total). The ether extracts are combined, washed three times with distilled water (2400 cc in total), dried over anhydrous sodium sulphate and filtered and the filtrate is concentrated under reduced pressure (20 mm Hg; 2.7 kPa) at 35° C. The product obtained (50 g) is chromatographed on neutral silica gel (500 g) contained in a column of diameter 5 cm; the column is eluted with a cyclohexane/ethyl acetate mixture (95/5 by volume; 2000 cc) and then with a cyclohexane/ethyl acetate mixture (90/10 by volume; 1000 cc), 500 cc fractions being collected. Fractions 3 and 4 are combined and concentrated to dryness under reduced pressure (20 mg Hg; 2.7 kPa) at 40° C.; a crystalline product (31 g) is thus obtained, which is used as such in the reaction described above. For identification in the pure state, this product (0.3 g) is redissolved in boiling diisopropyl ether (1.5 cc) and the solution obtained is cooled for 30 minutes at a temperature of about 0° C. The resulting crystals are filtered off, washed with diisopropyl ether (0.5 cc) and dried under reduced pressure (20 mm Hg; 2.7 kPa) at 20° C. 2-(Quinol-2-yl)-tetrahydrothiophen (0.2 g), melting at 63° C., is thus obtained.

Quinol-2-yl-methyl 3-chloropropyl sulphide can be prepared in the following manner:

A 10 N aqueous solution of sodium hydroxide (97 cc) is added dropwise, at 15° C. and in the course of 15 minutes, to a solution of 2-(quinol-2-yl-methyl)-isothiourea dihydrochloride (141 g) in distilled water (240 cc). After heating for 20 minutes at 73° C. and then cooling to 10° C., a 10 N aqueous solution of sodium hydroxide (60 cc) and then 1-bromo-3-chloropropane (81.5 g) are added, whilst stirring, and stirring is continued for 15 hours at a temperature of about 20° C. The reaction mixture is then extracted three times with methylene chloride (430 cc in total); the organic extracts are combined, washed with distilled water (250 cc) and dried over anhydrous sodium sulphate. After filtration, the solution obtained is poured onto neutral silica gel (250 g) contained in a column of diameter 4.3 cm; the column is then eluted with methylene chloride (1180 cc). The first fraction (700 cc) is discarded. The second fraction (480 cc) is collected and concentrated to dryness under reduced pressure (20 mm Hg; 2.7 kPa) at 35° C. Quinol-2-yl-methyl-3-chloropropyl sulphide (82 g) is thus obtained in the form of an orange oil.

[Rf=0.3; chromatography on a thin layer of silica gel; solvent: cyclohexane/ethyl acetate (50/50 by volume)].

2-(Quinol-2-yl-methyl)-isothiourea dihydrochloride can be prepared in the following manner:

A suspension, kept at 70° C., of 2-chloromethylquinoline hydrochloride (107 g) in ethanol (450 cc) is added dropwise and in the course of 15 minutes to a suspension of thiourea (45.5 g) in boiling ethanol (260 cc). The reaction mixture is stirred for 1 hour 30 minutes at the boil and then cooled to 20° C. The resulting crystals are filtered off, washed twice with ethanol (100 cc in total) and dried under reduced pressure (20 mm Hg; 2.7 kPa) at a temperature of about 20° C. 2-(Quinol-2-yl-methyl)-isothiourea dihydrochloride (141 g), melting at 250° C., is thus obtained.

EXAMPLE 4

A 33% (weight/volume) solution of methylamine in ethanol (7.5 cc) is added dropwise and in the course of 15 minutes to a solution of methyl 2-(pyrid-2-yl)-tetrahydrothiopyran-2-carbodithioate (9 g) in ethanol (60 cc), kept at a temperature of about 20° C. The solution is then stirred for 16 hours at a temperature of about 20° C. The resulting crystals are filtered off, washed twice with ethanol (20 cc in total) and dried under reduced pressure (20 mm Hg; 2.7 kPa) at a temperature of about 20° C. A crystalline crude product (7.8 g) is thus obtained, which is redissolved in boiling ethanol (96 cc); decolourising charcoal (0.4 g) is added to the solution thus obtained, which is filtered hot, and the filtrate is then cooled for 30 minutes at 0° C. The resulting crystals are filtered off, washed twice with ethanol (20 cc in total) and dried under reduced pressure (1 mm Hg; 0.13 kPa) at 45° C. N-Methyl-2-(pyrid-2-yl)-tetrahydrothiopyran-2-carbothioamide (6.3 g), melting at 153° C., is thus obtained.

Methyl 2-(pyrid-2-yl)-tetrahydrothiopyran-2-carbodithioate can be prepared in the following manner:

A mixture of anhydrous hexamethylphosphorotriamide and anhydrous tetrahydrofuran (47/53 by volume; 192 cc) is added dropwise, in the course of 10 minutes, to a 1.6 M solution of n-butyllithium in hexane (265 cc), kept under an argon atmosphere and at a temperature of about −60° C. A solution of 2-(pyrid-2-yl)-tetrahydrothiopyran (50.6 g) in a mixture of anhydrous hexamethylphosphorotriamide and anhydrous tetrahydrofuran (47/53 by volume; 192 cc) is then added in the course of 15 minutes and at the same temperature. After stirring for 5 minutes, a solution of carbon disulphide (32 g) in a mixture of anhydrous hexamethylphosphorotriamide and anhydrous tetrahydrofuran (47/53 by volume; 192 cc) is added in the course of 13 minutes. A solution of methyl iodide (60.5 g) in a mixture of anhydrous hexamethylphosphorotriamide and anhydrous tetrahydrofuran (47/53 by volume; 192 cc) is then added in the course of 15 minutes. The reaction mixture is subsequently stirred for 45 minutes at −65° C. and then for 2 hours, whilst allowing the temperature to rise gradually to 5° C. It is then run into a mixture of distilled water (1500 cc) and ethyl acetate (900 cc). After decantation, the aqueous phase is extracted with ethyl acetate (500 cc). The organic extracts are combined, washed three times with distilled water (4500 cc in total), dried over anhydrous sodium sulphate and filtered and the filtrate is concentrated to dryness under reduced pressure (20 mm Hg; 2.7 kPa) at 70° C. The product obtained (87 g) is chromatographed on neutral silica gel (800 g) contained in a column of diameter 6 cm; the column is eluted with a cyclohexane/ethyl acetate mixture (95/5 by volume; 5700 cc), one 1000 cc fraction, one 800 cc fraction, one 900 cc fraction and one 3000 cc fraction being collected. The last fraction is concentrated to dryness under reduced pressure (2 mm Hg; 2.7 kPa) at 50° C. The product obtained (24 g) is dissolved in boiling diisopropyl ether (100 cc); decolourising charcoal (0.4 g) is added to the solution, which is filtered hot, and the filtrate is then cooled for 1 hour at 0° C. The resulting crystals are filtered off, washed twice with diisopropyl ether (30 cc in total) and dried under reduced pressure (1 mm Hg; 0.13 kPa) at 35° C. Methyl 2-(pyrid-2-yl)-tetrahydrothiopyran-2-carbodithioate (14.5 g), melting at 79° C., is thus obtained.

2-(Pyrid-2-yl)-tetrahydrothiopyran can be prepared in the following manner:

A solution of pyrid-2-ylmethyl 4-chlorobutyl sulphide (82 g) in anhydrous tetrahydrofuran (100 cc) is added dropwise, in the course of 15 minutes and whilst keeping the temperature below 30° C., to a solution of potassium tert.-butoxide (66 g) in a mixture of anhydrous hexamethylphosphorotriamide (100 cc) and anhydrous tetrahydrofuran (530 cc). After stirring for 1 hour at a temperature of about 20° C., potassium tert.-butoxide (20 g) is added and stirring is continued for 45 minutes at the same temperature. The reaction mixture is added to a mixture of distilled water (1000 cc) and diethyl ether (600 cc); after decantation, the aqueous phase is extracted twice with diethyl ether (400 cc in total). The ether extracts are combined, washed three times with distilled water (3000 cc in total), dried over anhydrous sodium sulphate and filtered and the filtrate is concentrated under reduced pressure (20 mm Hg; 2.7 kPa) at 35° C. 2-(Pyrid-2-yl)-tetrahydrothiopyran (50.6 g) is thus obtained in the form of a brown oil.

[Rf=0.7; chromatography on a thin layer of silica gel; solvent:cyclohexane/ethyl acetate (50/50 by volume)].

Pyrid-2-ylmethyl 4-chlorobutyl sulphide can be prepared in the following manner:

A 10 N aqueous solution of sodium hydroxide (100 cc) is added dropwise, in the course of 20 minutes and whilst keeping the temperature below 15° C., to a solution of 2-(pyrid-2-ylmethyl)-isothiourea dihydrochloride (120 g) in distilled water (250 cc), cooled to 13° C. After heating for 20 minutes at 73° C. and then cooling to 13° C., a 10 N aqueous solution of sodium hydroxide (60 cc) and then 1-bromo-4-chlorobutane (85 g) are added, whilst stirring, and stirring is continued for 15 hours at a temperature of about 20° C. The reaction mixture is then extracted three times with methylene chloride (430 cc in total); the organic extracts are combined, washed with distilled water (300 cc); dried over anhydrous sodium sulphate and filtered. The solution is poured onto neutral silica gel (100 g) contained in a column of diameter 3 cm; the column is eluted with methylene chloride (3700 cc). The first fraction (700 cc) is discarded. The second (2000 cc) is concentrated to dryness under reduced pressure (20 mm Hg; 2.7 kPa) at 35° C. Pyrid-2-ylmethyl 4-chlorobutyl sulphide (82 g) is thus obtained.

[Rf=0.60; chromatography on a thin layer of silica gel; solvent:cyclohexane/ethyl acetate (50/50 by volume)].

2-(Pyrid-2-ylmethyl)-isothiourea dihydrochloride can be prepared in the following manner:

A solution of 2-chloromethylpyridine hydrochloride (30 g) in ethanol (100 cc), at 60° C., is added dropwise and in the course of 15 minutes to a suspension of thiourea (17.6 g) in boiling ethanol (100 cc). Boiling is maintained for 90 minutes and then, after cooling, the resulting crystals are filtered off, washed twice with ethanol (100 cc in total) and dried under reduced pressure (20 mm Hg; 2.7 kPa) at a temperature of about 20° C., in the presence of potassium hydroxide pellets. 2-(Pyrid-2-ylmethyl)isothiourea dihydrochloride (41.7 g), melting at 220° C., is thus obtained.

2-Chloromethylpyridine hydrochloride can be prepared in accordance with the method described in German Patent Application No. 1204231.

EXAMPLE 5

A solution of methyl 2-(pyrid-2-yl)-1,3-dithiane-2-carbodithioate (10.4 g) in a mixture of anhydrous diethyl ether and anhydrous ethanol (75/25 by volume; 690 cc) is saturated, at a temperature of the order of 20° C., for 45 minutes, by a stream of anhydrous ammonia gas. After stirring for 16 hours at the same temperature, further ammonia gas is introduced for 1 hour until saturation is reached. The resulting crystals are filtered off, washed twice with anhydrous diethyl ether (30 cc in total) and dried under reduced pressure (20 mm Hg; 2.7 kPa) at a temperature of about 20° C. A first fraction (6.2 g) of product is obtained. The filtrate is concentrated under reduced pressure (20 mm Hg; 2.7 kPa) at 50° C. After cooling, anhydrous diethyl ether (100 cc) is added to the residue obtained. The resulting crystals are filtered off, washed twice with anhydrous diethyl ether (30 cc in total) and dried under reduced pressure (20 mm Hg; 2.7 kPa) at a temperature of about 20° C. The product obtained (0.5 g) is dissolved in boiling acetonitrile (30 cc); the solution is filtered hot and the filtrate is then cooled to a temperature of about 0° C. The resulting crystals are filtered off, washed with acetonitrile (3 cc) and dried under reduced pressure (20 mm Hg; 2.7 kPa) at a temperature of about 20° C. A second fraction (0.4 g) is thus obtained. The two fractions (6.2 g and 0.4 g) are combined and dissolved in boiling acetonitrile (400 cc); the solution, to which decolourising charcoal (0.1 g) is added, is filtered hot and the filtrate is then cooled for 30 minutes at a temperature of about 0° C. The resulting crystals are filtered off, washed twice with acetonitrile (40 cc in total) and dried under reduced pressure (1 mm Hg; 0.13 kPa) at 55° C. 2-(Pyrid-2-yl)-1,3-dithiane-2-carbothioamide (5.5 g), melting at 214° C., is thus obtained.

Methyl 2-(pyrid-2-yl)-1,3-dithiane-2-carbodithioate can be prepared in the following manner:

A mixture of anhydrous hexamethylphosphorotriamide and anhydrous tetrahydrofuran (47/53 by volume; 140 cc) is added dropwise and in the course of 10 minutes to a 1.6 M solution of n-butyllithium in hexane (140 cc), kept under a nitrogen atmosphere and cooled to −60° C. A solution of 2-(pyrid-2-yl)-1,3-dithiane (36 g) in a mixture of anhydrous hexamethylphosphorotriamide and anhydrous tetrahydrofuran (47/53 by volume; 140 cc) is then added in the course of 20 minutes and at the same temperature. After stirring for 15 minutes, a solution of carbon disulphide (17 g) in a mixture of anhydrous hexamethylphosphorotriamide and anhydrous tetrahydrofuran (47/53 by volume; 70 cc) is added in the course of 10 minutes. After stirring for 5 minutes at −60° C., a solution of methyl iodide (32 g) in anhydrous hexamethylphosphorotriamide and anhydrous tetrahydrofuran (70 cc) is added in the course of 10 minutes. After stirring for 1 hour 30 minutes at a temperature of about −40° C., distilled water (500 cc) is added; the mixture is then extracted four times with ethyl acetate (1100 cc in total). The organic extracts are combined, washed three times with distilled water (1200 cc in total), dried over anhydrous sodium sulphate and filtered and the filtrate is concentrated to dryness under reduced pressure (20 mm Hg; 2.7 kPa) at 40° C. The product obtained (57 g) is chromatographed on neutral alumina (1080 g) contained in a column of diameter 5.2 cm. Elution is carried out with cyclohexane (6000 cc), 1000 cc fractions being collected, and then with a cyclohexane/ethyl acetate mixture (99/1 by volume; 2500 cc), 500 cc fractions being collected. Fractions 7 to 11 are combined and concentrated to dryness under reduced pressure (20 mm Hg; 2.7 kPa) at 40° C. The product obtained (15 g) is dissolved in boiling ethanol (30 cc) and the solution is cooled for 1 hour at 0° C. The resulting crystals are filtered off, washed twice with ethanol (20 cc in total) and dried under reduced pressure (20 mm Hg; 2.7 kPa) at a temperature of about 20° C. Methyl 2-(pyrid-2-yl)-1,3-dithiane-2-carbodithioate (7.7 g), melting at 91° C., is thus obtained.

2-(Pyrid-2-yl)-1,3-dithiane can be prepared in the following manner:

A solution of pyridine-2-carboxaldehyde (26.7 g), propane-1,3-dithiol (94.4 g) and paratoluenesulphonic acid (3.7 g) in 1,2-dichloroethane (2500 cc) is kept at the boil for 20 hours so that the water formed is removed by azeotropic distillation. After cooling to 5° C., the reaction mixture is washed twice with an approximately 7 N aqueous solution of potassium hydroxide (540 cc in total) and then four times with distilled water (1400 cc in total). The organic solution is dried over anhydrous sodium sulphate and filtered and the filtrate is concentrated under reduced pressure (20 mm Hg; 2.7 kPa) at 40° C. 2-(Pyrid-2-yl)-1,3-dithiane (41.9 g) is thus obtained.

[Rf=0.6; chromatography on a thin layer of silica gel; solvent: cyclohexane/ethyl acetate (50/50 by volume)].

EXAMPLE 6

A 33% (weight/volume) solution of methylamine in ethanol (6.5 cc) is added dropwise, in the course of 10 minutes and at a temperature between 34° C. and 37° C., to a solution of methyl 2-(pyrid-2-yl)-1,3-oxathiane-2-carbodithioate (17.5 g) in ethanol (60 cc). The reaction mixture is then stirred for 30 minutes at 2° C. The resulting crystals are filtered off, washed twice with petroleum ether (40 cc in total) and dried under reduced pressure (20 mm Hg; 2.7 kPa) at a temperature of about 20° C. The product obtained (13.4 g) is dissolved in boiling ethanol (80 cc); decolourising charcoal (0.2 g) is added to the solution, which is filtered hot, and the filtrate is then cooled for 1 hour at a temperature of about 0° C. The resulting crystals are filtered off, washed twice with ethanol (20 cc in total) and dried under reduced pressure (1 mm Hg; 0.13 kPa) at 50° C. N-Methyl-2-(pyrid-2-yl)-1,3-oxathiane-2-carbothioamide (12 g), melting at 157° C., is thus obtained.

Methyl 2-(pyrid-2-yl)-1,3-oxathiane-2-carbodithioate can be prepared in the following manner:

A mixture of anhydrous hexamethylphosphorotriamide and anhydrous tetrahydrofuran (47/53 by volume; 153 cc) is added dropwise and in the course of 15 minutes to a 1.6 M solution of n-butyllithium in hexane (212 cc), kept under a nitrogen atmosphere and cooled to a temperature of about −60° C. A solution of 2-(pyrid-2-yl)-1,3-oxathiane (34.4 g) in a mixture of anhydrous hexamethylphosphorotriamide and anhydrous tetrahydrofuran (47/53 by volume; 153 cc) is then added in the course of 25 minutes at the same temperature. After stirring for 15 minutes, a solution of carbon disulphide (23.3 g) in a mixture of anhydrous hexamethylphosphorotriamide and anhydrous tetrahydrofuran (47/53 by volume; 153 cc) is added in the course of 15 minutes. After stirring for 5 minutes at −70° C., a solution of methyl iodide (43.4 g) in anhydrous hexamethylphosphorotriamide and anhydrous tetrahydrofuran (47/53 by volume; 153 cc) is added in the course of 10 minutes. The reaction mixture is stirred for 45 minutes at −70° C. and then for 1 hour, whilst allowing the temperature to rise gradually to about 20° C. The reaction mixture is run into a mixture of distilled water (1200 cc) and ethyl acetate (800 cc). After decantation, the aqueous phase is extracted twice with ethyl acetate (1200 cc in total); the organic phases are combined, washed three times with distilled water (1500 cc in total), dried over anhydrous sodium sulphate and filtered and the filtrate is concentrated to dryness under reduced pressure (20 mm Hg; 2.7 kPa) at 45° C. The product obtained (69.3 g) is chromatographed on neutral silica gel (700 g) contained in a column of diameter 5.4 cm. Elution is carried out successively with cyclohexane (2300 cc), a cyclohexane/ethyl acetate mixture (98/2 by volume; 4000 cc), a cyclohexane/ethyl acetate mixture (95/5 by volume; 7000 cc) and a cyclohexane/ethyl acetate mixture (90/10 by volume; 3000 cc), a first 2300 cc fraction and then fourteen 1000 cc fractions being collected. Fractions 11 to 15 are combined and concentrated to dryness under reduced pressure (20 mm Hg; 2.7 kPa) at 45° C. Crude methyl 2-(pyrid-2-yl)-1,3-oxathiane-2-carbodithioate (17.5 g), melting at 116° C., is thus obtained.

2-(Pyrid-2-yl)-1,3-oxathiane can be prepared in the following manner:

A solution of pyridine-B 2-carboxaldehyde (26.7 g), 3-mercaptopropan-1-ol (81.1 g) and para-toluenesulphonic acid (3.7 g) in 1,2-dichloroethane (2500 cc) is kept at the boil for 15 hours so that the water formed is removed by azeotropic distillation. After cooling to a temperature of about 20° C., the reaction mixture is washed three times with a 5 N aqueous solution of sodium hydroxide (1200 cc in total) and then three times with distilled water (2400 cc in total). The organic phase is dried over anhydrous sodium sulphate and filtered and the filtrate is concentrated under reduced pressure (20 mm Hg; 2.7 kPa) at 50° C. 2-(Pyrid-2-yl)-1,3-oxathiane (36.6 g) is obtained in the form of a light brown oil.

[Rf=0.45; chromatography on a thin layer of silica gel; solvent: cyclohexane/ethyl acetate (50/50 by volume)].

3-Mercaptopropan-1-ol can be prepared as described in the literature [R. O. Clinton et al., J. Amer. Chem. Soc., 67, 594 (1945)].

EXAMPLE 7

A mixture of anhydrous hexamethylphosphorotriamide and anhydrous tetrahydrofuran (47/53 by volume; 225 cc) is added dropwise and in the course of 22 minutes to a 1.6 M solution of n-butyllithium in hexane (300 cc), kept under an argon atmosphere and at a temperature of about −60° C. A solution of 2-(pyrid-B 2-yl)-1,3-dithiane (56 g) in a mixture of anhydrous hexamethylphosphorotriamide and anhydrous tetrahydrofuran (47/53 by volume; 225 cc) is then added in the course of 30 minutes. After stirring for 15 minutes, a solution of methyl isothiocyanate (31 g) in a mixture of anhydrous hexamethylphosphorotriamide and anhydrous tetrahydrofuran (47/53 by volume; 225 cc) is added in the course of 15 minutes. The reaction mixture is subsequently stirred for 1 hour at −65° C. and then for 1 hour whilst allowing the temperature to rise gradually to about 20° C. It is then run into a mixture of distilled water (1500 cc) and ethyl acetate (1500 cc). After decantation, the aqueous solution is extracted twice with ethyl acetate (2500 cc in total). The organic extracts are combined, washed three times with distilled water (4500 cc in total), dried over anhydrous sodium sulphate and filtered and the filtrate is concentrated to dryness under reduced pressure (20 mm Hg; 2.7 kPa) at 50° C. The product obtained (90 g) is dissolved in boiling ethanol (600 cc) and the solution is cooled for 30 minutes at a temperature of about 5° C. The resulting crystals are filtered off, washed with ethanol (20 cc) and then twice with diisopropyl ether (40 cc in total) and dried under reduced pressure (20 mm Hg; 2.7 kPa) at a temperature of about 20° C. The product obtained (23.7 g) is combined with a product (0.7 g) prepared under the same conditions in another similar operation, and the combined product is dissolved in boiling ethanol (780 cc); decolourising charcoal (2.5 g) is added to the solution, which is filtered hot, and the filtrate is then cooled for 1 hour at a temperature of about 5° C. The resulting crystals are filtered off, washed twice with ethanol (50 cc in total) and then with diisopropyl ether (25 cc) and dried under reduced pressure (20 mm Hg; 2.7 kPa) at a temperature of about 20° C. The product thus obtained (19 g) is dissolved in boiling ethanol (600 cc); decolourising charcoal (5 g) is added to the solution, which is filtered hot, and the filtrate is then cooled for 15 hours at a temperature of about 5° C. The resulting crystals are filtered off, washed twice with ethanol (50 cc in total) and then with diisopropyl ether (25 cc) and dried under reduced pressure (1 mm Hg; 0.13 kPa) at 55° C. N-Methyl-2-(pyrid-2-yl)-1,3-dithiane-2-carbothioamide (15.9 g), melting at 159° C., is thus obtained.

EXAMPLE 8

A mixture of anhydrous hexamethylphosphorotriamide and anhydrous tetrahydrofuran (47/53 by volume; 70 cc) is added dropwise and in the course of 15 minutes to a 1.6 M solution of n-butyllithium in hexane (119 cc), kept under a nitrogen atmosphere and at a temperature of about −60° C. A solution of 2-pyrazinyltetrahydrothiophen (19.5 g) in a mixture of anhydrous hexamethylphosphorotriamide and anhydrous tetrahydrofuran (47/53 by volume; 70 cc) is then added in the course of 15 minutes. After stirring for 15 minutes, a solution of methyl isothiocyanate (12.7 g) in a mixture of anhydrous hexamethylphosphorotriamide and anhydrous tetrahydrofuran (47/53 by volume; 30 cc) is added in the course of 15 minutes. The reaction mixture is subsequently stirred for 45 minutes at −65° C. and then for 1 hour whilst allowing the temperature to rise gradually to about 20° C. It is then run into a mixture of ethyl acetate (300 cc) and distilled water (500 cc). After decantation, the aqueous solution is extracted twice with ethyl acetate (400 cc in total). The organic extracts are combined, washed three times with distilled water (1500 cc in total), dried over anhydrous sodium sulphate and filtered and the filtrate is concentrated under reduced pressure (20 mm Hg; 2.7 kPa) at 70° C. The product obtained (33.3 g) is chromatographed on neutral silica gel (330 g) contained in a column of diameter 4.2 cm. Elution is carried out successively with a cyclohexane/ethyl acetate mixture (90/10 by volume; 4000 cc) and then with a cyclohexane/ethyl acetate mixture (80/20 by volume; 7000 cc), 500 cc fractions being collected. Fractions 13 to 22 are combined and concentrated to dryness under reduced pressure (20 mm Hg; 2.7 kPa) at 60° C. The product obtained (11 g) is dissolved in a boiling mixture of propanol and diisopropyl ether (75/25 by volume; 48 cc); decolourising charcoal (0.2 g) is added to the solution, which is filtered hot, and the filtrate is then cooled for 18 hours at 5° C. The resulting crystals are filtered off, washed with a propanol/diisopropyl ether mixture (75/25 by volume; 10 cc) and dried under reduced pressure (1 mm Hg; 0.13 kPa) at 45° C. N-Methyl-2-pyrazinyltetrahydrothiophen-2-carbothioamide (4.9 g), melting at 127° C., is thus obtained.

2-Pyrazinyltetrahydrothiophen can be prepared in the following manner:

A solution of pyrazinylmethyl 3-chloropropyl sulphide (59 g) in anhydrous tetrahydrofuran (75 cc) is added dropwise, in the course of 15 minutes and whilst keeping the temperature below 30° C., to a solution of potassium tert.-butoxide (51 g) in a mixture of anhydrous hexamethylphosphorotriamide (75 cc) and anhydrous tetrahydrofuran (400 cc). After stirring for 30 minutes at the same temperature, potassium tert.-butoxide (10 g) is added and stirring is continued for 30 minutes. The reaction mixture is then run into a mixture of distilled water (800 cc) and diethyl ether (400 cc). After decantation, the aqueous phase is extracted twice with diethyl ether (300 cc in total). The organic extracts are combined, washed three times with distilled water (2400 cc in total), dried over anhydrous sodium sulphate and filtered and the filtrate is concentrated to dryness under reduced pressure (20 mm Hg; 2.7 kPa) at 35° C. The product obtained (30 g) is chromatographed on neutral silica gel (100 g) contained in a column of diameter 3 cm; the column is eluated with cyclohexane (750 cc), a cyclohexane/ethyl acetate mixture (90/10 by volume; 2500 cc) and ethyl acetate (500 cc), 250 cc fractions being collected. Fractions 4 to 15 are combined and concentrated to dryness under reduced pressure (20 mm Hg; 2.7 kPa) at 35° C. 2-Pyrazinyltetrahydrothiophen (19.5 g) is thus obtained in the form of a brown oil.

[Rf=0.52; chromatography on a thin layer of silica gel; solvent: cyclohexane/ethyl acetate (50/50 by volume)].

Pyrazinylmethyl 3-chloropropyl sulphide can be prepared in the following manner:

A 10 N aqueous solution of sodium hydroxide (39 cc) is added dropwise, in the course of 15 minutes and at a temperature of about 10° C., to a solution of 2-(pyrazinylmethyl)-isothiourea monohydrochloride (77.6 g) in distilled water (250 cc). After heating for 30 minutes at 70° C. and then cooling to 15° C., a 10 N aqueous solution of sodium hydroxide (47 cc) and then 1-bromo-3-chloropropane (66.5 g) are added and stirring is continued for 15 hours at a temperature of about 20° C. The reaction mixture is then extracted three times with methylene chloride (280 cc in total). The organic extracts are combined, washed twice with distilled water (200 cc in total), dried over anhydous sodium sulphate and filtered. The solution obtained is poured onto neutral silica gel (80 g) contained in a column of diameter 2.7 cm; the column is then eluted with methylene chloride (900 cc). The first fraction (300 cc) is discarded; the second fraction (600 cc) is collected and concentrated to dryness under reduced pressure (20 mm Hg; 2.7 kPa) at 35° C. Pyrazinylmethyl 3-chloropropyl sulphide (59 g) is thus obtained in the form of a yellow-orange oil.

[Rf=0.47; chromatography on a thin layer of silica gel; solvent: cyclohexane/ethyl acetate (50/50 by volume)].

2-(Pyrazinylmethyl)-isothiourea hydrochloride can be prepared in the following manner:

A solution of chloromethylpyrazine (88 g) in ethanol (200 cc) is added dropwise and in the course of 15 minutes to a suspension of thiourea (68 g) in boiling ethanol (370 cc). After stirring for 1 hour 30 minutes at the boil, the reaction mixture is cooled for 15 hours at a temperature of about 5° C. The resulting crystals are filtered off, washed twice with ethanol (120 cc) and dried under reduced pressure (20 mm Hg; 2.7 kPa) at a temperature of about 20° C. 2-(Pyrazinylmethyl)-isothiourea hydrochloride (74 g), melting at 183° C., is thus obtained.

Chloromethylpyrazine can be prepared as described in the literature [A. Hirschbert and P. Spoerri, J. Org. Chem., 26, 2356 (1961)].

EXAMPLE 9

A mixture of anhydrous hexamethylphosphorotriamide and anhydrous tetrahydrofuran (47/53 by volume; 80 cc) is added dropwise and in the course of 15 minutes to a 1.6 M solution of n-butyllithium in hexane (75 cc), kept under a nitrogen atomosphere and at a temperature of about −60° C. A solution of 2-(pyrid-2-yl)-tetrahydrofuran (15 g) in a mixture of anhydrous hexamethylphosphorotriamide and anhydrous tetrahydrofuran (47/53 by volume; 80 cc) is then added in the course of 20 minutes. After stirring for 30 minutes at the same temperature, a solution of methyl isothiocyanate (8.8 g) in a mixture of anhydrous hexamethylphosphorotriamide and anhydrous tetrahydrofuran (47/53 by volume; 80 cc) is added in the course of 20 minutes. The reaction mixture is subsequently stirred for 45 minutes at about −60° C. and then for 1 hour whilst allowing the temperature to rise gradually to about 20° C. It is then run into a mixture of distilled water (600 cc) and ethyl acetate (400 cc). After decantation, the aqueous solution is extracted twice with ethyl acetate (800 cc in total). The organic extracts are combined, washed three times with distilled water (1500 cc in total), dried over anhydrous sodium sulphate and filtered and the filtrate is concentrated under reduced pressure (20 mm Hg; 2.7 kPa) at 45° C. The product obtained (6.6 g) is dissolved in boiling diisopropyl ether (350 cc); decolourising charcoal (0.5 g) is added to the solution, which is filtered hot, and the filtrate is then cooled for 30 minutes at 0° C. The resulting crystals are filtered off, washed twice with diisopropyl ether (10 cc in total) and dried under reduced pressure (20 mm Hg; 2.7 kPa) at a temperature of about 20° C. The product obtained (7.7 g) is combined with a product (0.8 g) prepared under the same conditions, and the combined product is dissolved in boiling ethanol (30 cc); decolourising charcoal (0.2 g) is added to the solution, which is filtered hot, and the filtrate is then cooled for 1 hour at 0° C. The resulting crystals are filtered off, washed twice with ethanol (10 cc in total) and dried under reduced pressure (1 mm Hg; 0.13 kPa) at 45° C. N-Methyl-2-(pyrid-2-yl)-tetrahydrofuran-2-carbothioamide (6 g), melting at 115° C., is thus obtained.

2-(Pyrid-2-yl)-tetrahydrofuran can be prepared in the following manner:

A solution of 4-(1,1-dimethylpropoxy)-1-(pyrid-2-yl)-butan-1-ol (122 g) and para-toluenesulphonic acid (107.4 g) in toluene (1000 cc) is kept at the boil for 28 hours so that the water formed is removed by azeotropic distillation. After cooling to a temperature of about 20° C., distilled water (250 cc) is added. The organic phase is decanted and washed with distilled water (50 cc); the aqueous phases are combined and neutralised by adding sodium bicarbonate (49 g). The mixture is extracted three times with ethyl acetate (1500 cc in total). The organic extracts are combined and filtered and the filtrate is concentrated under reduced pressure (20 mm Hg; 2.7 kPa) at 40° C. A first oily fraction (30.8 g) is thus obtained. The aqueous phase previously obtained is re-extracted five times with methylene chloride (2500 cc in total); the organic extracts are combined, dried over anhydrous sodium sulphate and filtered and the filtrate is concentrated to dryness under reduced pressure (20 mm Hg; 2.7 kPa) at 35° C. A second oily fraction (11.2 g) is thus obtained. The two fractions (30.8 g and 11.2 g) are combined and run into polyphosphoric acid (200 g) at 80° C., in the course of 30 minutes. After stirring for 10 minutes at the same temperature and then cooling to a temperature of about 20° C., the reaction mixture is poured into distilled water (400 cc). A 10 N aqueous solution of sodium hydroxide (450 cc) is then added, whilst keeping the temperature below 20° C. The resulting crystals are filtered off and washed with ethyl acetate (500 cc). After separation of the filtrate by decantation, the aqueous phase is extracted three times with ethyl acetate (1500 cc in total). The organic extracts are combined, dried over anhydrous sodium sulphate and filtered and the filtrate is concentrated under reduced pressure (20 mm Hg; 2.7 kPa) at 40° C. 2-(Pyrid-2-yl)-tetrahydrofuran (26 g) is thus obtained.

[Rf=0.57; chromatography on a thin layer of silica gel; solvent: ethyl acetate].

4-(1,1-Dimethylpropoxy)-1-(pyrid-2-yl)-butan-1-ol can be prepared in accordance with the method described in the literature for 4-(1,1-dimethylpropoxy)-1-phenyl-butan-1-ol [W. B. Renfrow et al., J. Org. Chem., 26, 935 (1961)].

EXAMPLE 10

A mixture of anhydrous hexamethylphosphorotriamide and anhydrous tetrahydrofuran (47/53 by volume; 36 cc) is added dropwise and in the course of 15 minutes to a 1.6 M solution of n-butyllithium in hexane (55 cc), kept under a nitrogen atmosphere and at a temperature of about −60° C. A solution of 2-(pyridazin-3-yl)-tetrahydrothiophen (9.7 g) in a mixture of anhydrous hexamethylphosphorotriamide and anhydrous tetrahydrofuran (47/53 by volume; 36 cc) is then added in the course of 20 minutes. After stirring for 15 minutes at the same temperature, a solution of methyl isothiocyanate (6.4 g) in a mixture of anhydrous hexamethylphosphorotriamide and anhydrous tetrahydrofuran (47/53 by volume; 36 cc) is added in the course of 15 minutes. The reaction mixture is subsequently stirred for 1 hour at −65° C. and then for one hour whilst allowing the temperature to rise gradually to −10° C. It is then run into a mixture of distilled water (350 cc) and ethyl acetate (300 cc). After decantation, the aqueous solution is extracted with ethyl acetate (200 cc). The organic extracts are combined, washed three times with distilled water (900 cc in total), dried over anhydrous sodium sulphate and filtered and the filtrate is concentrated to dryness under reduced pressure (20 mm Hg; 2.7 kPa) at 55° C. The product obtained (12.4 g) is combined with a product (1 g) prepared under the same conditions, and the combined product is chromatographed on neutral silica gel (154 g) contained in a column of diameter 3.2 cm. The column is eluted with a cyclohexane/ethyl acetate mixture (90/10 by volume; 500 cc), a cyclohexane/ethyl acetate mixture (80/20 by volume; 1000 cc), a cyclohexane/ethyl acetate mixture (70/30 by volume; 2250 cc) and a cyclohexane/ethyl acetate mixture (50/50 by volume; 2500 cc), 250 cc fractions being collected. Fractions 19 to 25 are combined and concentrated to dryness under reduced pressure (20 mm Hg; 2.7 kPa) at 55° C. The product obtained (2.4 g) is dissolved in boiling ethanol (50 cc); decolourising charcoal (0.15 g) is added to the solution, which is filtered hot, and the filtrate is then cooled for 30 minutes at 0° C. The resulting crystals are filtered off, washed with ethanol (2 cc) and then twice with diisopropyl ether (6 cc in total) and dried under reduced pressure (1 mm Hg; 0.13 kPa) at 60° C. N-Methyl-2-(pyridazin-3-yl)-tetrahydrothiophen-2-carbothioamide (0.8 g), melting at 199° C., is thus obtained.

2-(Pyridazin-3-yl)-tetrahydrothiophen can be prepared in the following manner:

A solution of pyridazin-3-ylmethyl 3-chloropropyl sulphide (28.2 g) in anhydrous tetrahydrofuran (35 cc) is added dropwise, in the course of 15 minutes and whilst keeping the temperature below −20° C., to a solution of potassium tert.-butoxide (24 g) in a mixture of anhydrous hexamethylphosphorotriamide (35 cc) and anhydrous tetrahydrofuran (190 cc). The reaction mixture is subsequently stirred for 1 hour 30 minutes at −40° C. and is then run, at 0° C., into a mixture of distilled water (500 cc) and diethyl ether (500 cc). After decantation, the aqueous phase is extracted with diethyl ether (250 cc). The ether extracts are combined, washed three times with distilled water (1500 cc in total), dried over anhydrous sodium sulphate and filtered, and the filtrate is concentrated to dryness under reduced pressure (20 mm Hg; 2.7 kPa) at 30° C. 2-(Pyridazin-3-yl)-tetrahydrothiophen (10.5 g) is thus obtained in the form of a brown oil.

[Rf=0.4; chromatography on a thin layer of silica gel; solvent: ethyl acetate].

Pyridazin-3-ylmethyl 3-chloropropyl sulphide can be prepared in the following manner:

A 10 N aqueous solution of sodium hydroxide (84 cc) is added dropwise, in the course of 10 minutes and whilst keeping the temperature below 18° C., to a solution of 2-(pyridazin-3-ylmethyl)-isothiourea dihydrochloride (106 g) in distilled water (220 cc). After heating for 20 minutes at 75° C. and then cooling to 10° C., a 10 N aqueous solution of sodium hydroxide (50 cc) and then 1-bromo-3-chloropropane (69 g) are added, whilst stirring, and stirring is continued for 15 hours at a temperature of about 20° C. The reaction mixture is then extracted three times with methylene chloride (340 cc in total). The organic extracts are combined, washed with distilled water (250 cc) and dried over anhydrous sodium sulphate. After filtration, the solution obtained is poured onto neutral silica gel (80 g) contained in a column of diameter 2.7 cm; the column is then eluted with methylene chloride (700 cc). The first fraction (200 cc) is discarded. The second fraction (500 cc) is collected and concentrated to dryness under reduced pressure (20 mm Hg; 2.7 kPa) at 35° C. Pyridazin-3-ylmethyl 3-chloropropyl sulphide (60 g) is thus obtained in the form of a red oil.

[Rf=0.1; chromatography on a thin layer of silica gel; solvent: cyclohexane/ethyl acetate (50/50 by volume)].

2-(Pyridazin-3-ylmethyl)-isothiourea dihydrochloride can be prepared as described in the literature [K. YU. Novitskii et al., Khim. Geterotsikl. Soedin., (3) 412 (1970); C.A., 73, 25385z (1970)].

EXAMPLE 11

A mixture of anhydrous hexamethylphosphorotriamide and anhydrous tetrahydrofuran (47/53 by volume; 50 cc) is added dropwise and in the course of 10 minutes to a 1.6 M solution of n-butyllithium in hexane (44 cc), kept under a nitrogen atmosphere and cooled to −70° C. A solution of 2-(pyrid-3-yl)-1,3-oxathiane (8.5 g) in a mixture of anhydrous hexamethylphosphorotriamide and anhydrous tetrahydrofuran (47/53 by volume; 50 cc) is then added in the course of 25 minutes at the same temperature. After stirring for 15 minutes, a solution of methyl isothiocyanate (5.4 g) in a mixture of anhydrous hexamethylphosphorotriamide and anhydrous tetrahydrofuran (47/53 by volume; 50 cc) is added in the course of 15 minutes. The reaction mixture is stirred for 45 minutes at −70° C. and then for 1 hour whilst allowing the temperature to rise gradually to about 20° C. It is then run into a stirred mixture of distilled water (300 cc) and ethyl acetate (240 cc). After decantation, the aqueous phase is extracted twice with ethyl acetate (400 cc in total). The organic phases are combined, washed three times with distilled water (600 cc in total), dried over anhydrous sodium sulphate and filtered, and the filtrate is concentrated to dryness under reduced pressure (20 mm Hg; 2.7 kPa) at 50° C. The product obtained, to which a mixture of diisopropyl ether and ethyl acetate (90/10 by volume; 70 cc) is added, is stirred for 10 minutes at 20° C. The resulting crystals are filtered off, washed twice with diisopropyl ether (20 cc in total) and dried under reduced pressure (20 mm Hg; 2.7 kPa) at a temperature of about 20° C. The product obtained (4.4 g) is chromatographed on neutral silica gel (40 g) contained in a column of diameter 2.6 cm. Elution is carried out with a cyclohexane/ethyl acetate mixture (40/60 by volume; 2000 cc) and then with ethyl acetate (800 cc), 200 cc fractions being collected. Fractions 4 to 14 are combined and concentrated to dryness under reduced pressure (20 mm Hg; 2.7 kPa) at 50° C. The product obtained (3.9 g) is dissolved in boiling acetonitrile (45 cc). The solution, to which decolourising charcoal (0.2 g) is added, is filtered hot and the filtrate, after cooling, is then kept for 1 hour at 0° C. The resulting crystals are filtered off, washed twice with acetonitrile (10 cc in total) and dried under reduced pressure (1 mm Hg; 0.13 kPa) at 60° C. N-Methyl-2-(pyrid-3-yl)-1,3-oxathiane-2-carbothioamide (2.9 g), melting at 194° C., is thus obtained.

2-(Pyrid-3-yl)-1,3-oxathiane can be prepared in the following manner:

A solution of pyridine-3-carboxaldehyde (16 g), 3-mercaptopropan-1-ol (48 g) and para-toluenesulphonic acid (2.25 g) in 1,2-dichloroethane (1500 cc) is kept at the boil for 15 hours so that the water formed is removed by azeotropic distillation. After cooling to a temperature of about 20° C., the reaction mixture is washed three times with a 5 N aqueous solution of sodium hydroxide (750 cc in total) and then three times with distilled water (1500 cc in total). The organic phase is dried over anhydrous sodium sulphate and filtered, and the filtrate is concentrated to dryness under reduced pressure (20 mm Hg; 2.7 kPa) at 50° C. The product obtained (15.6 g) is chromatographed in neutral silica gel (200 g) contained in a column of diameter 3.7 cm. Elution is carried out successively with a cyclohexane/ethyl acetate mixture (80/20 by volume; 600 cc) and a cyclohexane/ethyl acetate mixture (70/30 by volume; 2700 cc), 300 cc fractions being collected. Fractions 5 to 11 are combined and concentrated to dryness under reduced pressure (20 mm Hg; 2.7 kPa) at 50° C. 2-(Pyrid-3-yl)-1,3-oxathiane (8.6 g) is thus obtained in the form of a yellow oil.

(Rf=0.6; chromatography on a thin layer of silica gel; solvent: ethyl acetate).

3-Mercaptopropan-1-ol can be prepared as described in the literature [R. O. Clinton et al., J. Amer. Chem. Soc., 67 594 (1945)].

EXAMPLE 12

A solution of diisopropylamine (101 g) in a mixture of anhydrous hexamethylphosphorotriamide and anhydrous tetrahydrofuran (47/53 by volume; 225 cc) is added dropwise, in the course of 10 minutes, to a 1.6 M solution of n-butyllithium in hexane (625 cc), kept under a nitrogen atmosphere and cooled to −60° C. After stirring for 10 minutes, a solution of pyrid-3-ylmethyl 4-chlorobutyl sulphide (84 g) in a mixture of anhydrous hexamethylphosphorotriamide and anhydrous tetrahydrofuran (47/53 by volume; 300 cc) is added in the course of 30 minutes at the same temperature. The reaction mixture is stirred for 1 hour at a temperature of about −65° C. and a solution of methyl isothiocyanate (117 g) in a mixture of anhydrous hexamethylphosphorotriamide and anhydrous tetrahydrofuran (47/53 by volume; 225 cc) is then run in at this temperature in the course of 20 minutes. The mixture is subsequently stirred for 30 minutes at −60° C. and then for 1 hour whilst allowing the temperature to rise gradually to 10° C. After adding distilled water (1 liter), the mixture is extracted six times with ethyl acetate (5 liters in total). The organic extracts are combined, washed five times with distilled water (5 liters in total), dried over anhydrous sodium sulphate and filtered and the filtrate is concentrated to dryness under reduced pressure (30 mm Hg; 4 kPa) at 40° C. The product obtained (167 g) is chromatographed on neutral silica gel (1500 g) contained in a column of diameter 7.4 cm.

The impurities are removed by eluting with a mixture of cyclohexane and ethyl acetate (about 50 liters), the ethyl acetate content of which varies progressively from 0 to 30%. Elution is then carried out with pure ethyl acetate, three 1 liter fractions and then eight 0.7 liter fractions being collected. These last 8 fractions are combined and concentrated to dryness under reduced pressure (20 mm Hg; 2.7 kPa) at 60° C. The product obtained (20 g) is dissolved in a boiling mixture of diisopropyl ether (80 cc) and ethanol (40 cc). After cooling for 1 hour at 0° C., the resulting crystals are filtered off, washed with diisopropyl ether (25 cc) and dried under reduced pressure (20 mm Hg; 2.7 kPa) at a temperature of about 20° C. The product (14.2 g) is dissolved in boiling acetonitrile (43 cc); the solution, to which decolourising charcoal (0.8 g) is added, is filtered hot and the filtrate, after cooling, is kept for 45 minutes at a temperature of about 5° C. The resulting crystals are filtered off, washed with acetonitrile (4 cc) and then twice with diisopropyl ether (8 cc in total). After drying under reduced pressure (1 mm Hg; 0.13 kPa) at 60° C., N-methyl-2-(pyrid-3-yl)-tetrahydrothiopyran-2-carbothioamide (10.6 g), melting at 131° C., is obtained.

Pyrid-3-ylmethyl 4-chlorobutyl sulphide can be prepared in the following manner:

A 10 N aqueous solution of sodium hydroxide (144 cc) is added dropwise, in the course of 25 minutes and whilst keeping the temperature below 12° C., to a solution of 2-(pyrid-3-ylmethyl)-isothiourea dihydrochloride (173 g) in distilled water (330 cc), cooled to 4° C. After heating for 25 minutes at 70° C. and then cooling to 11° C., a 10 N aqueous solution of sodium hydroxide (89 cc) and then 1-bromo-4-chlorobutane (123.5 g) are added, whilst stirring, and stirring is continued for 15 hours at a temperature of about 20° C. The reaction mixture is then extracted four times with methylene chloride (560 cc in total); the organic extracts are combined, washed twice with distilled water (800 cc in total), dried over anhydrous sodium sulphate and filtered. The solution is poured onto neutral silica gel (150 g) contained in a column of diameter 3.7 cm; the column is eluted with methylene chloride (2500 cc). The first fraction (600 cc) is discarded. The second (2500 cc) is concentrated to dryness under reduced pressure (25 mm Hg; 3.4 kPa) without exceeding 30° C. Pyrid-3-ylmethyl 4-chlorobutyl sulphide (110 g) is thus obtained.

[Rf=0.31; chromatography on a thin layer of silica gel; solvent: cyclohexane/ethyl acetate (50/50 by volume)].

2-(Pyrid-3-ylmethyl)-isothiourea dihydrochloride can be prepared in the following manner:

A solution of 3-chloromethylpyridine hydrochloride (164 g) in ethanol (510 cc), at 50° C., is added dropwise and in the course of 20 minutes to a solution of thiourea (91 g) in boiling ethanol (510 cc). The reaction mixture is stirred for 3 hours 50 minutes at the boil and then cooled to 26° C. The resulting crystals are filtered off, washed twice with ethanol (400 cc in total) and dried under reduced pressure (25 mm Hg; 2.7 kPa) at a temperature of about 20° C. 2-(Pyrid-3-ylmethyl)-isothiourea dihydrochloride (173 g), melting at 212° C., is thus obtained.

EXAMPLE 13

A solution of diisopropylamine (9.6 g) in a mixture of anhydrous hexamethylphosphorotriamide and anhydrous tetrahydrofuran (47/53 by volume; 22 cc) is added dropwise, in the course of 11 minutes, to a 1.6 M solution of n-butyllithium in hexane (59 cc), kept under a nitrogen atmosphere and cooled to −50° C. A solution of quinol-3-ylmethyl 3-chloropropyl sulphide (9.2 g) in a mixture of anhydrous hexamethylphosphorotriamide and anhydrous tetrahydrofuran (47/53 by volume; 28 cc) is then added in the course of 20 minutes at a temperature of about −60° C. The reaction mixture is stirred for 30 minutes at the same temperature and a solution of methyl isothiocyanate (11.1 g) in a mixture of anhydrous hexamethylphosphorotriamide and anhydrous tetrahydrofuran (47/53 by volume; 22 cc) is then run in over the course of 15 minutes. The mixture is stirred for a further 25 minutes at −65° C. and then for 30 minutes whilst allowing the temperature to rise gradually to 10° C. After adding distilled water (100 cc), the mixture is extracted three times with ethyl acetate (300 cc in total). The organic extracts are combined, washed five times with distilled water (500 cc in total), dried over anhydrous sodium sulphate and concentrated to dryness under reduced pressure (20 mm Hg; 2.7 kPa) at 60° C. The product obtained (20 g) is chromatographed on neutral silica gel (30 g) contained in a column of diameter 3.8 cm.

Elution is carried out successively with a mixture of cyclohexane and ethyl acetate (1200 cc), the ethyl acetate content of which varies progressively from 0 to 10%, with a cyclohexane/ethyl acetate mixture (90/10 by volume; 2400 cc), with a cyclohexane/ethyl acetate mixture (85/15 by volume; 1080 cc), with a cyclohexane/ethyl acetate mixture (80/20 by volume; 1080 cc) and with a cyclohexane/ethyl acetate mixture (70/30 by volume; 1440 cc), 120 cc fractions being collected. Fractions 51, 52 and 53 are combined and concentrated to dryness under reduced pressure (20 mm Hg; 2.7 kPa) at 55° C. The product obtained (1.3 g) is dissolved in boiling ethanol (17 cc); decolourising charcoal (0.4 g) is added to the solution, which is then filtered hot, and the filtrate, after cooling, is kept for 3 hours at a temperature of about 5° C. The resulting crystals are filtered off, washed with ethanol (1 cc) and twice with diisopropyl ether (2 cc in total). After drying under reduced pressure (1 mm Hg; 0.13 kPa) at 40° C., N-methyl-2-(quinol-3-yl)-tetrahydrothiophen-2-carbothioamide (0.8 g), melting at 159° C., is obtained.

Quinol-3-ylmethyl 3-chloropropyl sulphide can be prepared in the following manner:

A 10 N aqueous solution of sodium hydroxide (40.8 cc) is added in the course of 9 minutes, and whilst allowing the temperature to rise to 10° C., to a solution, cooled to 1° C., of 2-(quinol-3-ylmethyl)-isothiourea dihydrochloride (59.2 g) in distilled water (100 cc). After heating for 20 minutes at a temperature of about 70° C. and then cooling to 12° C., a 10 N aqueous solution of sodium hydroxide (25 cc) is added dropwise in the course of 5 minutes. 1-Bromo-3-chloropropane (33.6 g) is then added and stirring is continued for 20 hours at a temperature of about 20° C. The reaction mixture is then extracted three times with methylene chloride (400 cc in total). The organic extracts are combined, washed with distilled water (100 cc), dried over anhydrous sodium sulphate and concentrated under reduced pressure (20 mm Hg; 2.7 kPa) at 35° C. so as to bring the volume to about 100 cc. The solution thus obtained is chromatographed on neutral silica gel (250 g) contained in a column of diameter 3.8 cm. Elution is carried out with methylene chloride (1500 cc), one 600 cc fraction and one 900 cc fraction being collected. The latter fraction is concentrated to dryness under reduced pressure (20 mm Hg; 2.7 kPa) at 35° C. Quinol-3-ylmethyl 3-chloropropyl sulphide (9.2 g) is thus obtained in the form of a yellow oil.

(Rf=0.6; chromatography on a thin layer of silica gel; solvent: ethyl acetate).

2-(Quinol-3-ylmethyl)-isothiourea dihydrochloride can be prepared in the following manner:

A solution of 3-chloromethylquinoline hydrochloride (46.4 g) in ethanol (160 cc), at 70° C., is added dropwise, in the course of 10 minutes, to a suspension of thiourea (19.7 g) in boiling ethanol (110 cc). The reaction mixture is stirred for 1 hour 30 minutes at the boil and then cooled to 10° C. The resulting crystals are filtered off, washed twice with ethanol (100 cc in total) and dried under reduced pressure (20 mm Hg; 2.7 kPa) at a temperature of about 20° C. 2-(Quinol-3-ylmethyl)-isothiourea dihydrochloride (59.3 g), melting at 226°-228° C., is thus obtained.

3-Chloromethylquinoline hydrochloride can be prepared in accordance with the method described by J. Kotler-Brajtburg, Acta. Pol. Pharm., 25 (4), 383 (1968); C.A., 70 87518s.

The present invention includes within its scope pharmaceutical compositions which comprise, as active ingredient, at least one of the thioformamide derivatives of general formula I in association with one or more compatible and pharmaceutically acceptable carriers or adjuvants. The carriers or adjuvants may themselves be physiologically active. The invention includes especially preparations made up for oral, parenteral or rectal administration.

Tablets, pills, powders (especially in gelatin capsules or in cachets) or granules can be used in solid compositions for oral administration. In these compositions, the active compound according to the invention is admixed with one or more inert diluents such as starch, cellulose, sucrose, lactose or silica. These compositions can also comprise substances other than diluents, e.g. one or more lubricants, such as magnesium stearate or talc, a colorant, a coating (for coated tablets) or a varnish.

Solutions, suspensions, emulsions, syrups and pharmaceutically acceptable elixirs containing inert diluents, such as water, ethanol, glycerol, vegetable oils or paraffin oil, can be used as liquid compositions for oral administration. These compositions can also comprise substances other than diluents, for example wetting agents, sweeteners, thickeners, flavourings or stabilisers.

Sterile compositions for parenteral administration are preferably suspensions, emulsions or aqueous or non-aqueous solutions. Water, propylene glycol, a polyethylene glycol, vegetable oils, in particular olive oil, injectable organic esters, e.g. ethyl oleate, or other suitable organic solvents can be employed as the solvent or vehicle. These compositions can also contain adjuvants, in particular wetting agents, isotonising agents, emulsifiers, dispersing agents and stabilisers. Sterilisation can be carried out in several ways, for example by aseptic filtration, by incorporating sterilising agents into the composition, by irradiation or by heating. The compositions can also be prepared in the form of sterile solid compositions which can be dissolved in an injectable liquid sterile medium immediately before use.

Compositions for rectal administration are suppositories or rectal capsules, which contain, in addition to the active compound, excipients such as cacao butter, semi-synthetic glycerides or polyethylene glycols.

In human therapy, the thioformamide derivatives of the invention are particularly useful in the treatment of gastrointestinal ulcers and in the treatment of hypertension, depending on the definition of the symbol Het given hereinbefore. The doses depend on the desired effect and the duration of the treatment; for an adult, they are generally between 25 and 1000 mg per day, administered orally in one or more portions.

In general, the physician will decide the posology considered most appropriate, taking into account the age, weight and all the other factors intrinsic to the patient being treated.

The following Examples illustrate pharmaceutical compositions according to the invention.

EXAMPLE 14

Tablets containing a 50 mg dose of active product and having the following composition are prepared in accordance with the usual technique:
N-methyl-2-(pyrid-2-yl)-1,3-dithiane-2-carbothioamide: 50 mg;
starch: 60 mg;
lactose: 50 mg;
magnesium stearate: 2 mg.

EXAMPLE 15

Tablets containing a 25 mg dose of active product and having the following composition are prepared in accordance with the usual technique:
N-methyl-2-(pyrid-3-yl)-tetrahydrothiopyran-2-carbothioamide: 25 mg;
starch: 60 mg;
colloidal silica: 50 mg;
magnesium stearate: 2 mg.

We claim:

1. A thioformamide derivative of the formula:

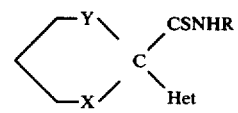

wherein R represents a hydrogen atom or an alkyl radical of 1 through 4 carbon atoms, and (i) Het represents a heterocyclic radical of aromatic character, containing one or two nitrogen atoms, selected from the group consisting of pyrid-3-yl, pyrid-4-yl, pyridazinyl, pyrazinyl, pyrimidinyl, quinolyl, imidazolyl, naphthyridinyl, quinoxalinyl and quinazolinyl, X represents a sulphur or oxygen atom and Y represents a sulphur or oxygen atom, a valency bond or a methylene radical, or (ii) Het represents the pyrid-2-yl radical, X represents a sulphur or oxygen atom and Y represents a sulphur or oxygen atom or a methylene radical, or (iii) Het represents the pyrid-2-yl radical, X represents an oxygen atom and Y represents a valency bond.

2. A thioformamide derivative according to claim 1 wherein Het represents a heterocyclic radical of aromatic character, containing one or two nitrogen atoms, which is attached in the α-position to this (or one of these) nitrogen atom (or atoms) and is selected from the group consisting of pyridazin-3-yl, pyrazinyl, pyrimidin-2-yl, pyrimidin-4-yl, quinol-2-yl, imidazol-2-yl, imidazol-4-yl, 1,8-naphthyridin-2-yl, quinoxal-2-yl, quinazol-2-yl and quinazol-4-yl, X represents a sulphur or oxygen atom, and Y represents a sulphur or oxygen atom, a valency bond or a methylene radical or, Het represents the pyrid-2-yl radical, X represents a sulphur or oxygen atom and Y represents a sulphur or oxygen atom or a methylene radical, or Het represents a pyrid-2-yl radical, X represents an oxygen atom and Y represents a valency bond.

3. A thioformamide derivative according to claim 2 wherein Het represents pyrid-2-yl, quinol-2-yl or pyradazin-3-yl.

4. A thioformamide derivative according to claim 1 wherein Het represents a heterocyclic radical of aromatic character, containing one or two nitrogen atoms, which is attached in the β-position to this (or one of these) nitrogen atom (or atoms) and is selected from the group consisting of pyrid-3-yl, pyridazin-4-yl, pyrimidin-5-yl, quinol-3-yl, imidazol-5-yl and 1,8-naphthyridin-3-yl, X represents a sulphur or oxygen atom, and Y represents a sulphur or oxygen atom, a valency bond or a methylene radical.

5. A thioformamide derivative according to claim 4 wherein Het represents pyrid-3-yl or quinol-3-yl.

6. A thioformamide derivative according to any one of claims 1, 2, 3, 4 or 5 wherein R represents the methyl radical.

7. A thioformamide derivative according to claim 1 which is N-methyl-2-(pyrid-3-yl)-tetrahydrothiophen-2-carbothioamide.

8. A thioformamide derivative according to claim 1 which is N-methyl-2-(quinol-2-yl)-tetrahydrothiophen-2-carbothioamide.

9. A thioformamide derivative according to claim 1 which is N-methyl-2-(pyrid-2-yl)-tetrahydrothiopyran-2-carbothioamide.

10. A thioformamide derivative according to claim 1 which is 2-(pyrid-2-yl)-1,3-dithiane-2-carbothioamide.

11. A thioformamide derivative according to claim 1 which is N-methyl-2-(pyrid-2-yl)-1,3-dithiane-2-carbothioamide.

12. A thioformamide derivative according to claim 1 which is N-methyl-2-(pyrid-2-yl)-tetrahydrofuran-2-carbothioamide.

13. A thioformamide derivative according to claim 1 which is N-methyl-2-(pyridazin-3-yl)-tetrahydrothiophen-2-carbothioamide.

14. A thioformamide derivative according to claim 1 which is N-methyl-2-(pyrid-3-yl)-1,3-oxathiane-2-carbothioamide.

15. A thioformamide derivative according to claim 1 which is N-methyl-2-(pyrid-3-yl)-tetrahydrothiopyran-2-carbothioamide.

16. A thioformamide derivative according to claim 1 which is N-methyl-2-(quinol-3-yl)-tetrahydrothiophen-2-carbothioamide.

17. A pharmaceutical composition useful in the treatment of gastrointestinal ulcers or hypertension which comprises, as active ingredient, an effective amount of a thioformamide derivative of the formula depicted in claim 1, wherein R, Het, X and Y are as defined in claim 1, in association with one or more compatible and pharmaceutically acceptable carriers or adjuvants.

18. A method for the treatment of a patient with gastrointestinal ulcers which comprises administering to the patient an effective amount to ameliorate the condition of the patient of a thioformamide derivative as claimed in claim 2 or 3.

19. A method for the treatment of a patient with hypertension which comprises administering to the patient an effective amount to ameliorate the condition of the patient of a thioformamide derivative as claimed in claim 4 or 5.

* * * * *